(12) United States Patent
Schiller et al.

(10) Patent No.: US 10,398,849 B2
(45) Date of Patent: Sep. 3, 2019

(54) INJECTION AID FOR USE WITH AN INJECTION DEVICE AND METHOD OF USE

(71) Applicant: BRISTOL-MYERS SQUIBB COMPANY, Princeton, NJ (US)

(72) Inventors: Eric Schiller, Westfield, NJ (US);
Prashant Kakade, Princeton, NJ (US);
Hiroo Noguchi, Tokyo (JP); Takuji Harada, Tokyo (JP); Hideo Fukushima, Tokyo (JP)

(73) Assignee: BRISTOL-MYERS SQUIBB COMAPNY, Princeton, NJ (US)

( * ) Notice: Subject to any disclaimer, the term of this patent is extended or adjusted under 35 U.S.C. 154(b) by 133 days.

(21) Appl. No.: 14/910,375

(22) PCT Filed: Jul. 28, 2014

(86) PCT No.: PCT/US2014/048417
§ 371 (c)(1),
(2) Date: Feb. 5, 2016

(87) PCT Pub. No.: WO2015/020823
PCT Pub. Date: Feb. 12, 2015

(65) Prior Publication Data
US 2016/0184531 A1  Jun. 30, 2016

Related U.S. Application Data

(60) Provisional application No. 61/863,229, filed on Aug. 7, 2013.

(51) Int. Cl.
*A61M 5/32* (2006.01)
*A61M 5/31* (2006.01)

(52) U.S. Cl.
CPC ........ *A61M 5/3204* (2013.01); *A61M 5/3287* (2013.01); *A61M 2005/3139* (2013.01);
(Continued)

(58) Field of Classification Search
CPC .............. A61M 5/3287; A61M 5/3202; A61M 5/3204; A61M 5/3205; A61M 5/321;
(Continued)

(56) References Cited

U.S. PATENT DOCUMENTS 5,242,426 A * 9/1993 Pituch ................. A61M 5/3213
206/365
5,445,619 A * 8/1995 Burns ................. A61M 5/3216
128/919
(Continued)

FOREIGN PATENT DOCUMENTS

CN    103189082 A    7/2013
EP    1331018        7/2003
(Continued)

OTHER PUBLICATIONS

International Search Report and Written Opinion for Int. App. No. PCT/US2014/048417, completed Nov. 12, 2014.

*Primary Examiner* — Shefali D Patel
*Assistant Examiner* — Tezita Z Watts
(74) *Attorney, Agent, or Firm* — McDonnell Boehnen Hulbert & Berghoff LLP (57) ABSTRACT

An injection aid for use with an injection device, such as a safety syringe, for example, is disclosed. The injection aid employs a flexible clip-based design to compensate for manufacturing tolerances associated with the injection device. The injection aid includes a body and a lever mounted to the body, the lever being configured to rotate about the body. The injection aid may further include gears rotate with rotation of the lever, and which function to remove a needle shield from the injection device. The body positions the injection device so as to ensure consistent injection depth.

22 Claims, 5 Drawing Sheets

(52) U.S. Cl.
CPC . *A61M 2205/581* (2013.01); *A61M 2205/583* (2013.01); *A61M 2205/584* (2013.01)

(58) Field of Classification Search
CPC ........ A61M 5/1626; A61M 2005/3139; A61M 2005/3208; A61M 2005/2437; A61M 2005/244; A61M 2205/581; A61M 2205/583; A61M 2205/584; A61M 2039/1066; A61M 414/729; A61M 206/365

See application file for complete search history.

(56) References Cited

U.S. PATENT DOCUMENTS

| | | | | |
|---|---|---|---|---|
| 5,603,699 | A | * | 2/1997 | Shine ................ A61M 5/3216 604/110 |
| 5,713,876 | A | * | 2/1998 | Bogert .............. A61M 25/0631 604/187 |
| 6,623,459 | B1 | | 9/2003 | Doyle |
| 8,057,431 | B2 | * | 11/2011 | Woehr ................ A61M 5/3216 604/110 |
| 2003/0167021 | A1 | | 9/2003 | Shimm |
| 2005/0022806 | A1 | | 2/2005 | Beaumont et al. |
| 2005/0049561 | A1 | | 3/2005 | Hommann et al. |
| 2007/0073224 | A1 | | 3/2007 | Dries |
| 2012/0035542 | A1 | * | 2/2012 | Pongprairochana .... A61M 5/20 604/110 |

FOREIGN PATENT DOCUMENTS

| | | | |
|---|---|---|---|
| EP | 2578188 | | 4/2013 |
| JP | H04-504671 | A | 8/1992 |
| JP | 2004-528151 | A | 9/2004 |
| JP | 2007-520247 | A | 7/2007 |
| JP | 2011-098133 | | 5/2011 |
| JP | 2011098133 | A * | 5/2011 |
| JP | 2011098133 | A * | 5/2011 |
| WO | 90/13328 | A1 | 11/1990 |
| WO | 02/100469 | A2 | 12/2002 |
| WO | 2004/098687 | | 11/2004 |
| WO | 2005/002654 | A2 | 1/2005 |

* cited by examiner

INJECTION AID FOR USE WITH AN INJECTION DEVICE AND METHOD OF USE

CROSS-REFERENCE TO RELATED APPLICATIONS

The present application is a U.S. National Phase Application pursuant to 35 U.S.C. § 371 of International Application No. PCT/US2014/048417 filed Jul. 28, 2014, which claims priority to U.S. Provisional Patent Application No. 61/863,229 filed Aug. 7, 2013. The entire disclosure contents of these applications are herewith incorporated by reference into the present application.

BACKGROUND

A. Field

This disclosure relates generally to injection devices and more particularly to an injection aid for use with an injection device to enhance ease and accuracy of administration of an injection, including self-administration of an injection.

B. Description of Related Art

A variety of devices for facilitating injection of medicament into a human or animal subject are known in the art. Some current injection devices include a safety device, such as a needle guard, coupled with a syringe to reduce the chances of accidental needle sticks and to facilitate safer disposal of the syringe.

A relatively large compressive force is exerted on the plunger of the syringe by the syringe barrel to provide for a tight, leak-proof seal. This quality of the seal, as well as the viscosity of the drug, gauge of the needle, and self-injector's dexterity, can make the movement of the plunger difficult. Typically, a user applies three fingers on one hand during the injection process to overcome/exert these forces: the thumb which exerts a force on the plunger rod and the index and middle fingers which hold the barrel or needle guard of the syringe. Barrels and needle guards may include a finger grip or flange to facilitate controlling the rate of movement of the plunger relative to the syringe. Often, the small surface area of the finger grips is not easily handled by a user with low dexterity. Further, the possibility exists that the needle shield (cover) may be pulled at an angle, which may result in the needle bending and/or breaking. There is also difficulty in achieving consistent injection depth, especially in self-injection scenarios.

Thus, it would be desirable to provide an injection aid to improve patient experience related to self-injection, such that the injection aid ensures adequate and consistent exposed needle length for injection (to target subcutaneous delivery). It would also be desirable to provide an injection aid that provides a comfortable user interface to the patient in terms of handling and injecting, with more surface area for steadier handling. It would further be desirable to provide an injection aid that always removes the needle shield in the axial direction so the needle is less prone to bending or breaking.

SUMMARY

The following embodiments and aspects thereof are described and illustrated in conjunction with systems, tools and methods which are meant to be exemplary and illustrative, not limiting in scope.

In one aspect, an injection aid for use with an injection device is described. The injection device has a needle shield. The injection aid includes a body being configured to receive the injection device, a lever mounted to the body and being configured to rotate about the body, and at least two gears mounted to the body. Each gear has at least one grip, and the grips are configured to apply force along a length of the needle shield. One of the at least two gears is connected to the lever. The grips are further configured to remove the needle shield when the lever is rotated from a fully open position to a fully closed position.

In another aspect, an injection aid for use with an injection device is disclosed. The injection aid includes a body being configured to receive the injection device, and at least two clips mounted to the body. The clips are configured to hold the injection device within the body. The clips are positioned on the body based on a manufacturing tolerance of the injection device.

In yet another aspect, an injection assembly is disclosed. An injection assembly includes a pre-filled syringe having a barrel and a plunger, a needle guard surrounding the barrel of the syringe, the needle guard being movable between a retracted position and an extended position, a housing for the needle guard having a finger flange, a flange extender located around the housing, a needle shield, and an injection aid. The injection aid includes a body being configured to receive the injection device, a lever mounted to the body and being configured to rotate about the body, and at least two gears mounted to the body. Each gear has at least one grip, and the grips are configured to apply force along a length of the needle shield. One of the at least two gears is connected to the lever. The grips are configured to remove the needle shield when the lever is rotated from a fully open position to a fully closed position.

In yet another aspect, a method of using an injection device with an injection aid includes providing an injection device having a needle shield, a plunger, and a flange extender, and providing an injection aid having a body, a lever mounted to the body, and at least two gears mounted to the body. Each gear has at least one grip, and the grips are configured to apply force along a length of the needle shield. The method also includes rotating the lever counterclockwise to a fully open position, placing the injection device within the injection aid, and rotating the lever clockwise to a fully closed position. Rotating the lever causes the gears to rotate, and as the gears rotate the grips of the gears grasp the needle shield along a circumference of the needle shield, and pull down along the length of the needle shield to automatically pull the needle shield off of the needle.

In addition to the exemplary aspects and embodiments described above, further aspects and embodiments will become apparent by reference to the drawings and by study of the following detailed description.

BRIEF DESCRIPTION OF THE DRAWINGS

Exemplary embodiments are illustrated in the drawings. It is intended that the embodiments and figures disclosed herein are to be considered illustrative rather than restrictive.

DETAILED DESCRIPTION

An injection aid for use with an injection device, such as a safety syringe, for example, is disclosed. The injection aid employs a flexible clip-based design to compensate for manufacturing tolerances associated with the injection device. The injection aid includes a body and a lever mounted to the body. The body positions the injection device so as to ensure consistent injection depth.

Figure 1:
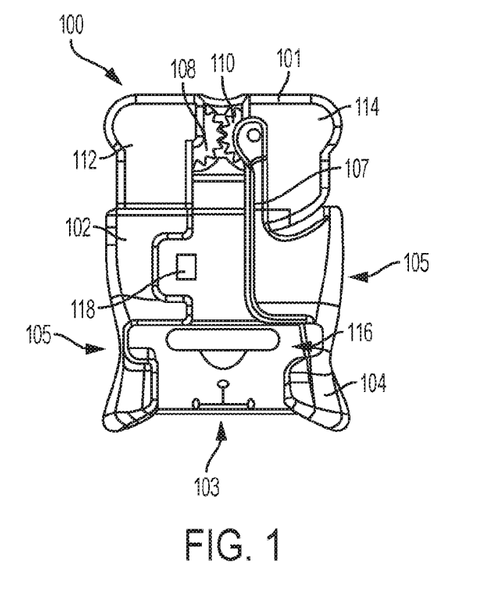
FIG. 1 is a front view of an injection aid of the present application.
Figure 6:
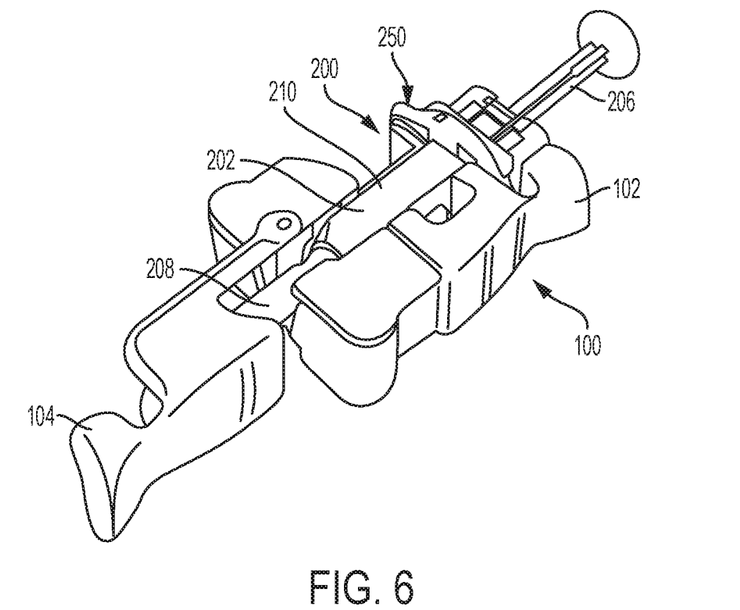
FIG. 6 is a perspective view of the injection aid of FIG. 1 in use with an injection device and shown in the open position.
Figure 7:
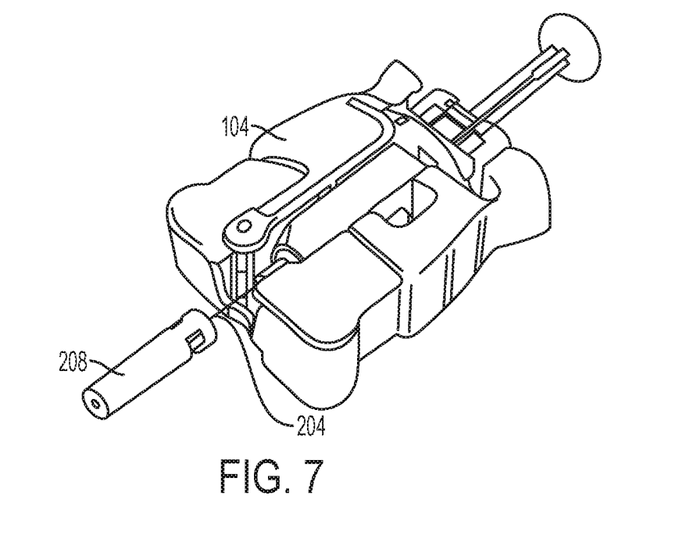
FIG. 7 is a perspective view of the injection aid of FIG. 1 in use with an injection device and shown in the closed position.
Figure 8:
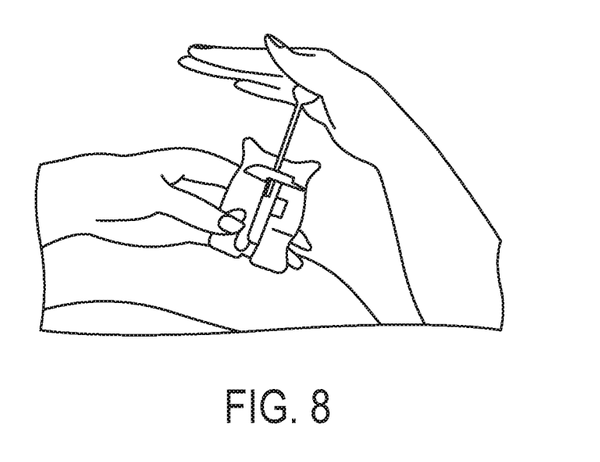
FIGS. 8 and 9 show the use of the injection aid in self-administration of an injection.
Figure 9:
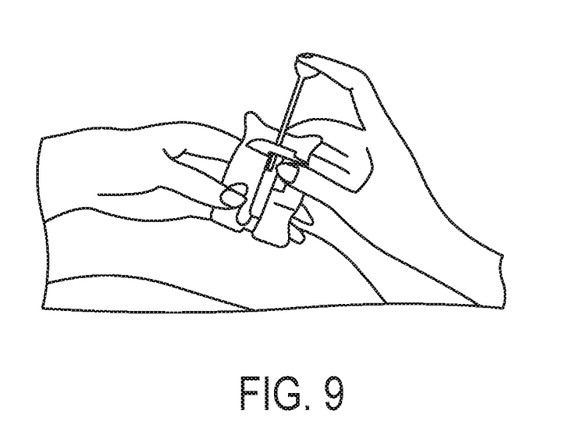

FIG. 1 shows an example injection aid 100 for use with an injection device, such as an injection device or pre-filled syringe 200 (shown in FIGS. 6-7). The injection device 200 is disposable and used only once in conjunction with the injection aid 100; the injection aid is reusable. To that end, the disposable injection device 200 is inserted into the injection aid and locked into place as shown in FIGS. 6 and 7, and in this condition (FIG. 7) the injection aid 100 facilitates the administration of an injection as shown in FIGS. 8 and 9. Injection device 200 will be described in more detail below.

Figure 2:
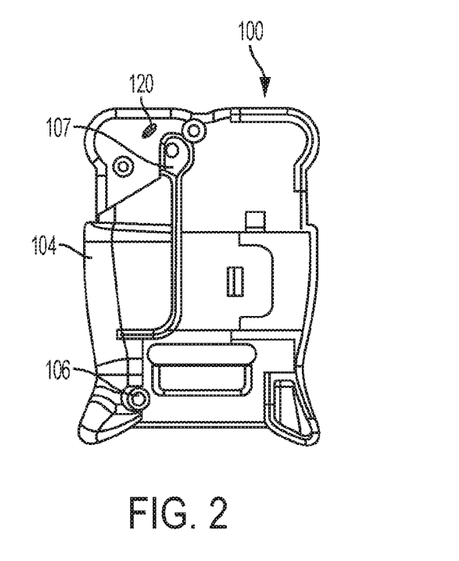
FIG. 2 is a rear view of the injection aid shown in FIG. 1.

The injection aid 100 includes a body 102 having an upper end 101 and a lower end 103. The body 102 further includes two sides 105 located between the upper end 101 and lower end 103. A lever 104 is mounted to a side 105 of the body 102. In one embodiment, the lever 104 is fixed to the body 102 by legs 107 mounted to the front and back of the injection aid 100. However, additional configurations of the lever are possible. The lever 104 rotates from a fully open position (shown in FIG. 6) to a fully closed position (shown in FIG. 7). Referring to FIG. 2, the body 102 may further include a locking feature 106 to lock the lever 104 onto the body 102 when the injection device is properly assembled in the injection aid 100. The locking feature 106 may provide audible feedback to a user to indicate that the lever 104 is in the fully closed and locked position.

Referring again to FIG. 1, two gears 108, 110 are mounted toward the upper end 101 of the body 102. Each gear has a plurality of teeth 109. Gear 110 is connected to the lever 104. Rotation of the lever 104 rotates the gears 108, 110, which in turn removes the needle shield off the injection device, which will be described in more detail below. Two cover parts 112, 114 hold the gears 108, 110 in place, and also prevent ingress of foreign objects into the injection aid 100.

Figure 5:
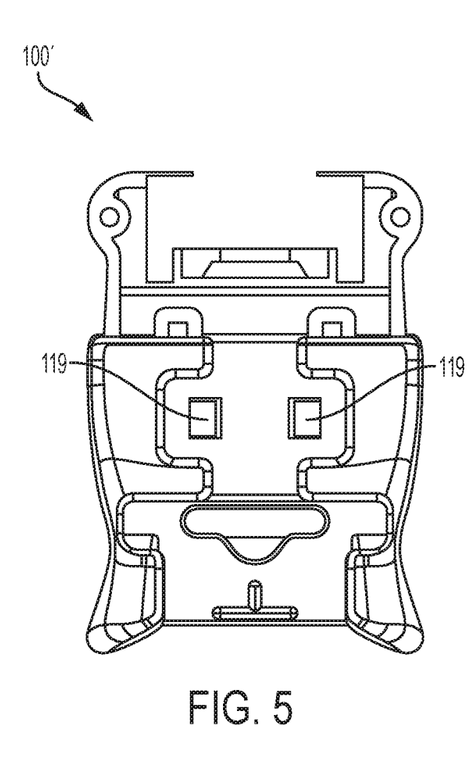
FIG. 5 is a second embodiment of an injection aid of the present application.

The injection aid 100 also includes one or more securing features for holding the injection device 200. In one embodiment, a notch 116 is present near the lower end 103 of the body 102 for accommodating the flange and/or flange extender portion of the injection device 200. Further, a clip 118 is mounted to the body 102 to securely hold the injection device 200 in place within the injection aid 100. It should be understood that the clip 118 may be mounted in a different area of the body 102 depending upon the particular manufacturing tolerances of the injection device used with the injection aid. Alternatively or additionally, more than one clip may be present, as shown in FIG. 5. Other securing features may be present as well.

Figure 3:
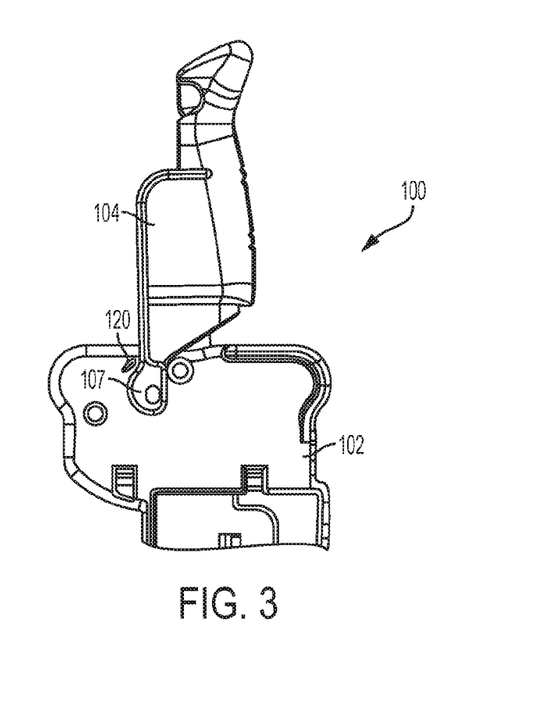
FIG. 3 is a perspective view of the lever of the injection aid of FIG. 1 shown in the open position.

Referring to FIG. 3, the injection aid 100 may further include a feature, such as arm 120, which holds the lever 104 in the open position, and thus facilitates the assembly of injection device 200 into the injection aid. Other features that can hold the lever 104 in the open position are possible as well.

Figure 4:
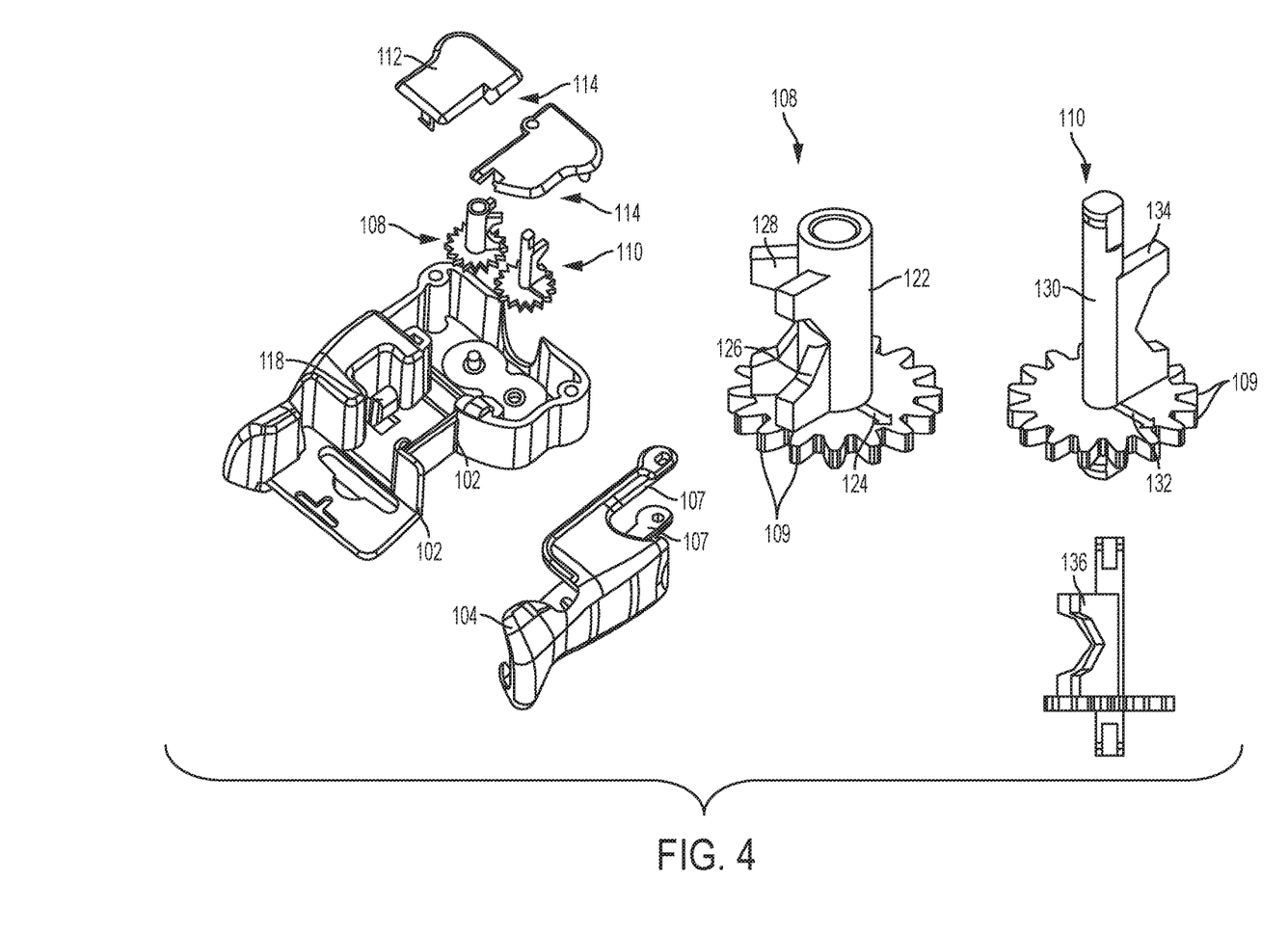
FIG. 4 is an exploded view of the injection aid shown in FIG. 1.

Referring now to FIG. 4, an exploded view of the injection aid 100 is provided. It can be seen that each gear includes a visual feedback feature, such as an arrow 124, 132 etched onto the gear. The arrows 124, 132 function to notify a user when the lever 104 is in the fully open position by pointing toward each other in the fully open position. In another embodiment, the visual feedback feature may include a coloring of a specific section of the gears, and the colors would line up when the lever 104 is in the fully open position.

Each gear 108, 110 further includes a shaft 122, 130, and two grips 126, 128 and 134, 136 along the shafts. It should be understood that more or less grips may be included on the shafts. In one embodiment, the grips 126, 128 and 134, 136 may be polygonal-shaped. In another embodiment, the grips 126, 128 and 134, 136 may have a circular shape. The rotation of the gears 108, 110, due to the movement of lever 104, moves the grips 128, 130 up or down the needle shield 208. The opposite grips of the two gears 108, 110 form an octagonal shape. Thus, the two grips on each of the gears together form an octagonal shape. Alternatively, the grips may take other shapes, as long as the grips apply force along the length of the needle shield. The grips 126, 128 and 134, 136 remove the needle shield, as explained in detail below.

FIG. 5 shows an alternative embodiment of an injection aid 100' having two securing features (clips 119) for holding the injection device 200. Alternatively, more or less securing features could be present. The injection aid 100' is not shown as including the needle cover removal feature, but it should be understood that a needle cover removal feature may be included.

FIGS. 6-7 show an example injection device 200 having a flange extender 250 for use with the injection aid 100 of the present application. The injection device 200 may include a safety device such as a safety shield or needle guard 202 surrounding a syringe body or barrel (shown as reference number 92 in FIG. 1 of U.S. Pat. No. 6,623,459 which is incorporated by reference). In one example, the injection device 200 and needle guard 202 may be in accordance with U.S. Pat. Nos. 6,623,459 and 7,255,689, which are both assigned to Safety Syringes, Inc., and which are incorporated by reference herein in their entireties. The needle guard 202 is movable between a retracted position in which the needle guard does not cover the needle 204 (shown in FIG. 6), and an extended position in which the needle guard covers the needle. The injection device 200 further includes a plunger 206. A user can apply a force to the plunger 206 to administer medication contained in the syringe. The injection device 200 further includes a needle shield 208 to cover the needle 204.

The needle guard 202 may also include a housing _210 having finger flanges (shown as reference number 96 in FIG. 1 of U.S. Pat. No. 6,623,459 which is incorporated by reference) which facilitate controlling the rate of movement of the plunger 206 relative to the syringe. The flange extender 250 surrounds opposite sides of the finger flanges. The flange extender 250 is described in detail in U.S. Pat. Pub. No. 2013/0018325 filed Jul. 11, 2011, entitled "Flange Extender for Use With an Injection Device and Method of Assembly," which is fully incorporated by reference herein.

In operation, the injection aid 100 may be sanitized before use. Next, a user opens the lever 104 by rotating the lever in a counter-clockwise direction. The arrows 124, 132 on the gears 108, 110 will point toward each other to indicate when the lever 104 has reached the fully open position (180°). The fully open position is shown in FIG. 6.

When the lever is fully opened, the injection device 200 is placed into the injection aid body 102. The notch 114 in the body provides directional guidance for the placement of the injection device 200. The clip 118 further secures the device 200 in place. The lever 104 is then closed by rotating the lever 104 in a clockwise direction. The rotating lever causes the two gear parts 108, 110 to rotate. As the gears rotate, the grips 126, 128 and 134, 136 along the gear shaft rotate as well. As the grips are rotating, they grasp the needle shield along its circumference and pull down along the length of the needle shield 208 until the needle shield is automatically pulled off the needle. The octagonal shape of the grips 126, 128 and 134, 136 ensures that the grips have sufficient contact area with the needle shield 208 no matter how the needle shield is rotated along the needle axis. Thus, the grips can pull off the needle shield irrespective of the angular orientation of the needle shield along the needle axis.

Once the needle shield 208 is pulled off, the lever 104 is closed by rotating the lever 104 completely in the clockwise direction over piece 106 until a soft, audible click is heard. The injection may then be administered by holding or grasping the injection aid 100 with one hand and compressing the plunger 206 with a finger of same hand or another hand, as shown in FIGS. 8 and 9. The needle 204 should be inserted perpendicularly against the skin. After injection, the needle 204 retracts automatically. The lever 104 is again opened to remove and dispose of the used injection device 200. The injection aid 100 may be cleaned and reused for future injections.

The injection aid 100 may be constructed of a plastic, such as Polycarbonate resin, for example. In other embodiments, the injection aid 100 may be constructed of other suitable materials.

While a number of exemplary aspects and embodiments have been discussed above, those of skill in the art will recognize that still further modifications, permutations, additions and sub-combinations thereof of the features of the disclosed embodiments are still possible. It is therefore intended that the following appended claims and claims hereafter introduced are interpreted to include all such modifications, permutations, additions and sub-combinations as are within their true spirit and scope.

The invention claimed is:

1. An injection aid for use with an injection device, the injection device having a needle shield positioned on a needle, the injection aid comprising:
a body being configured to receive a body of the injection device;
a lever mounted to the body of the injection aid, the lever being configured to rotate about the body of the injection aid; and
at least two cooperating gears mounted to the body of the injection aid, each gear having teeth and at least one grip, the at least one grip of each of the at least two gears being configured to apply force along a length of the needle shield, wherein one of the at least two gears is directly connected to the lever such that rotation of the lever causes the at least two cooperating gears to rotate so as to also rotate the at least one grip of each of the at least two gears;
wherein the at least one grip of each of at least two gears are configured to directly grasp and remove the needle shield when the lever is rotated from a fully open position to a fully closed position.

2. The injection aid of claim 1 further comprising at least one clip for securing the injection device within the body of the injection aid.

3. The injection aid of claim 2 wherein the at least one clip is positioned based on a manufacturing tolerance of the injection device.

4. The injection aid of claim 1 wherein the body of the injection aid further comprises a notch for receiving a flange of the injection device.

5. The injection aid of claim 1 wherein the at least one grip has a polygonal shape.

6. The injection aid of claim 1 wherein the at least one grip has a circular shape.

7. The injection aid of claim 1 wherein the at least two grips of each of the at least two gears together form an octagonal shape.

8. The injection aid of claim 1 wherein the injection device includes a flange extender.

9. The injection aid of claim 1 further comprising a feature located on the body of the injection aid to hold the lever in the open position.

10. The injection aid of claim 1 wherein the at least two gears each include a visual feedback feature to notify a user when the lever is in the fully open position.

11. The injection aid of claim 1 wherein the body of the injection aid further includes a locking feature for locking the lever onto the body of the injection aid in the fully closed position.

12. The injection aid of claim 11 wherein the locking feature provides audible feedback.

13. An injection assembly comprising:
a pre-filled syringe having a barrel and a plunger;
a needle guard surrounding the barrel of the syringe, the needle guard being movable between a retracted position and an extended position;
a housing for the needle guard having a finger flange;
a flange extender located around the housing;
a needle shield; and
an injection aid comprising:
a body being configured to receive the pre-filled syringe;
a lever mounted to the body, the lever being configured to rotate about the body; and
at least two cooperating gears mounted to the body, each gear having teeth and at least one grip, the at least one grip of each of the at least two gears being configured to apply force along a length of the needle shield, wherein one of the at least two gears is directly connected to the lever such that rotation of the lever causes the at least two cooperating gears to rotate so as to also rotate the at least one grip of each of the at least two gears;
wherein the at least one grip of each of the at least two gears are configured to directly grasp and remove the needle shield when the lever is rotated from a fully open position to a fully closed position.

14. The injection assembly of claim 13 wherein the body further comprises a notch for receiving the flange extender of the injection assembly.

15. The injection aid of claim 13 further comprising at least one clip for securing the pre-filled syringe within the body.

16. The injection assembly of claim 13 wherein at least two grips of each of the at least two gears together form an octagonal shape.

17. A method of using an injection device with an injection aid, the method comprising:
providing the injection device having a needle shield, a plunger, and a flange extender;
providing the injection aid having a body, a lever mounted to the body, and at least two cooperating gears mounted to the body, each gear having teeth and at least one grip, the at least one grip of each of the at least two gears being configured to apply force along a length of the needle shield, and one of the at least two cooperating gears being directly connected to the lever;
rotating the lever to a fully open position;
placing the injection device within the injection aid; and
rotating the lever to a fully closed position;
wherein rotating the lever causes the at least two cooperating gears rotate, and wherein as the gears rotate, the at least one grip of each of the at least two gears grasp the needle shield along a circumference of the needle shield, and the at least one grip of each of the at least two gears pull down along the length of the needle shield to automatically pull the needle shield off of a needle.

18. The method of claim 17 wherein an angle of the lever with respect to the body in the fully open position is 180 degrees.

19. The method of claim 17 wherein the lever is held in the fully open position by a feature positioned on the body.

20. The method of claim 17 wherein the lever is locked in the fully closed position by a locking feature.

21. The method of claim 17 further comprising:
grasping the injection aid with one hand;
compressing the plunger to perform an injection;
rotating the lever to the fully open position; and
removing the injection device.

22. The injection aid of claim 1 wherein the lever is configured to rotate about a transverse plane relative to a longitudinal axis of the injection device.

* * * * *

UNITED STATES PATENT AND TRADEMARK OFFICE
CERTIFICATE OF CORRECTION

PATENT NO. : 10,398,849 B2
APPLICATION NO. : 14/910375
DATED : September 3, 2019
INVENTOR(S) : Eric Schiller et al.

Page 1 of 1

It is certified that error appears in the above-identified patent and that said Letters Patent is hereby corrected as shown below:

In the Claims

Column 6, Line 16, Claim 7, delete "the" after "wherein"

Column 7, Line 16, Claim 17, insert --to-- after the first instance of "gears"

Signed and Sealed this
Fourteenth Day of January, 2020

Andrei Iancu
*Director of the United States Patent and Trademark Office*